United States Patent [19]
Hettiarachchi et al.

[11] Patent Number: 5,774,516
[45] Date of Patent: *Jun. 30, 1998

[54] MODIFICATION OF OXIDE FILM ELECTRICAL CONDUCTIVITY TO MAINTAIN LOW CORROSION POTENTIAL IN HIGH-TEMPERATURE WATER

[75] Inventors: Samson Hettiarachchi, Menlo Park, Calif.; Young J. Kim, Clifton Park; Peter L. Andresen, Schenectady, both of N.Y.; Thomas P. Diaz, San Martin, Calif.

[73] Assignee: General Electric Company, Schenectady, N.Y.

[ * ] Notice: The term of this patent shall not extend beyond the expiration date of Pat. No. 5,608,766.

[21] Appl. No.: 698,178

[22] Filed: Aug. 15, 1996

Related U.S. Application Data

[63] Continuation-in-part of Ser. No. 265,598, Jun. 24, 1994, abandoned, which is a continuation-in-part of Ser. No. 209,175, Mar. 10, 1994, abandoned, which is a continuation-in-part of Ser. No. 143,513, Oct. 29, 1993, abandoned, and a continuation-in-part of Ser. No. 143,514, Oct. 29, 1993, Pat. No. 5,448,605.

[51] Int. Cl.⁶ ................................................ G21C 9/00
[52] U.S. Cl. ........................... 376/305; 376/306; 422/11; 422/14; 422/19
[58] Field of Search .................................. 376/301, 305, 376/306, 356, 357; 422/11, 14, 19

[56] References Cited

U.S. PATENT DOCUMENTS

| | | | |
|---|---|---|---|
| 3,923,688 | 12/1975 | Hammel et al. | 252/432 |
| 4,555,275 | 11/1985 | Tobin | 148/6.3 |
| 4,828,790 | 5/1989 | Honda et al. | 376/306 |
| 5,028,384 | 7/1991 | Skarpelos et al. | 376/306 |
| 5,130,080 | 7/1992 | Niedrach | 376/305 |
| 5,130,081 | 7/1992 | Niedrach | 376/305 |
| 5,135,709 | 8/1992 | Andresen et al. | 376/305 |
| 5,164,152 | 11/1992 | Kim et al. | 376/305 |
| 5,377,245 | 12/1994 | Uetake et al. | 376/305 |
| 5,608,766 | 3/1997 | Andresen et al. | 376/305 |

*Primary Examiner*—Kathryn L. Gorgos
*Assistant Examiner*—Chrisman D. Carroll
*Attorney, Agent, or Firm*—Nixon & Vanderhye

[57] ABSTRACT

A method for mitigating general corrosion and crack initiation and growth on the surface of a metal components in a water-cooled nuclear reactor. A compound containing a non-noble metal such as zirconium or titanium is injected into the water of the reactor in the form of a solution or suspension. This compound decomposes under reactor thermal conditions to release ions or atoms of the non-noble metal which incorporate in the surfaces of the components, including the interior surfaces of any cracks formed therein. The preferred compounds are zirconium compounds such as zirconium acetylacetonate, zirconium nitrate and zirconyl nitrate. Zirconium incorporated in the oxided surface of a metal component will reduce the electrochemical corrosion potential at the surface to a level below the critical potential to protect against intergranular stress corrosion cracking without the addition of hydrogen.

22 Claims, 5 Drawing Sheets

MODIFICATION OF OXIDE FILM ELECTRICAL CONDUCTIVITY TO MAINTAIN LOW CORROSION POTENTIAL IN HIGH-TEMPERATURE WATER

RELATED PATENT APPLICATIONS

This application is a continuation-in-part application of U.S. patent application Ser. No. 08/265,598, filed 24 Jun., 1994 (incorporated herein by reference), now abandoned, which in turn a continuation-in-part application of U.S. patent application Ser. No. 08/209,175 filed on Mar. 10, 1994, now abandoned, which is in turn a continuation-in-part application of both U.S. patent application Ser. No. 08/143,513, now abandoned, and Ser. No. 08/143,514, filed on Oct. 29, 1993, now U.S. Pat. No. 5,448,605 (all incorporated herein by reference).

FIELD OF THE INVENTION

This invention relates to reducing the corrosion potential of components exposed to high-temperature water. As used herein, the term "high-temperature water" means water having a temperature of about 150° C. or greater, steam, or the condensate thereof. High-temperature water can be found in a variety of known apparatus, such as water deaerators, nuclear reactors, and steam-driven power plants.

BACKGROUND OF THE INVENTION

Nuclear reactors are used in electric power generation, research and propulsion. A reactor pressure vessel contains the reactor coolant, i.e. water, which removes heat from the nuclear core. Respective piping circuits carry the heated water or steam to the steam generators or turbines and carry circulated water or feedwater back to the vessel. Operating pressures and temperatures for the reactor pressure vessel are about 7 Mpa and 288° C. for a boiling water reactor (BVWR), and about 15 Mpa and 320° C. for a pressurized water reactor (PVVR). The materials used in both BVWRs and PWRs must withstand various loading, environmental and radiation conditions.

Some of the materials exposed to high-temperature water include carbon steel, alloy steel, stainless steel, and nickel-based, cobalt-based and zirconium-based alloys. Despite careful selection and treatment of these materials for use in water reactors, corrosion occurs on the materials exposed to the high-temperature water. Such corrosion contributes to a variety of problems, e.g., stress corrosion cracking, crevice corrosion, erosion corrosion, sticking of pressure relief valves and buildup of the gamma radiation-emitting Co-60 isotope.

Stress corrosion cracking (SCC) is a known phenomenon occurring in reactor components, such as structural members, piping, fasteners, and welds, exposed to high-temperature water. As used herein, SCC refers to cracking propagated by static or dynamic tensile stressing in combination with corrosion at the crack-tip. The reactor components are subject to a variety of stresses associated with, e.g. differences in thermal expansion, the operating pressure needed for the containment of the reactor cooling water, and other sources such as residual stress from welding, cold working and other asymmetric metal treatments. In addition, water chemistry, welding, crevice geometry, heat treatment, and radiation can increase the susceptibility of metal in a component to SCC.

It is well known that SCC occurs at higher rates when oxygen is present in the reactor water in concentrations of about 1 to 5 ppb or greater. SCC is increased in a high radiation flux where oxidizing species, such as oxygen, hydrogen peroxide, and short-lived radicals, are produced from radiolytic decomposition of the reactor water. Such oxidizing species increase the electrochemical corrosion potential (ECP) of metals. Electrochemical corrosion is caused by a flow of electrons from anodic to cathodic areas on metallic surfaces. The ECP is a measure of the thermodynamic tendency for corrosion phenomena to occur, and is a fundamental parameter in determining rates of, e.g., SCC, corrosion fatigue, corrosion film thickening and general corrosion.

In a BWR, the radiolysis of the primary water coolant in the reactor core causes the net decomposition of a small fraction of the water to the chemical products $H_2$, $H_2O_2$, $O_2$ and oxidizing and reducing radicals. For steady-state operating conditions, equilibrium concentrations of $O_2$, $H_2O_2$, and $H_2$ are established in both the water which is recirculated and the steam going to the turbine. This concentration of $O_2$, $H_2O_2$, and $H_2$ is oxidizing and results in conditions that can promote intergranular stress corrosion cracking (IGSCC) of susceptible materials of construction. One method employed to mitigate IGSCC of susceptible material is the application of hydrogen water chemistry (HWC), whereby the oxidizing nature of the BWR environment is modified to a more reducing condition. This effect is achieved by adding dissolved hydrogen to the reactor feedwater. When the hydrogen reaches the reactor vessel, it reacts with the radiolytically formed oxidizing species on metal surfaces to reform water, thereby lowering the concentration of dissolved oxidizing species in the water in the vicinity of metal surfaces. The rate of these recombination reactions is dependent on local radiation fields, water flow rates and other variables.

The injected hydrogen reduces the level of oxidizing species in the water, such as dissolved oxygen, and as a result lowers the ECP of metals in the water. However, factors such as variations in water flow rates and the time or intensity of exposure to neutron or gamma radiation result in the production of oxidizing species at different levels in different reactors. Thus, varying amounts of hydrogen have been required to reduce the levels of oxidizing species sufficiently to maintain the ECP below a critical potential required for protection from IGSCC in high-temperature water. As used herein, the term "critical potential" means a corrosion potential at or below a range of values of about −230 to −300 mV based on the standard hydrogen electrode (SHE) scale. IGSCC proceeds at an accelerated rate in systems in which the ECP is above the critical potential, and at a substantially lower rate in systems in which the ECP is below the critical potential. Water containing oxidizing species such as oxygen increases the ECP of metals exposed to the water above the critical potential, whereas water with little or no oxidizing species present results in an ECP below the critical potential.

Corrosion potentials of stainless steels in contact with reactor water containing oxidizing species can be reduced below the critical potential by injection of hydrogen into the feedwater. For adequate feedwater hydrogen addition rates, conditions necessary to inhibit IGSCC can be established in certain locations of the reactor. Different locations in the reactor systems require different levels of hydrogen addition. Much higher hydrogen injection levels are necessary to reduce the ECP within the high radiation flux of the reactor core, or when oxidizing cationic impurities, e.g., cupric ion, are present.

It has been shown that IGSCC of Type 304 stainless steel (containing 18–20% Cr, 8–10.5% Ni and 2% Mn) used in BBWRs can be mitigated by reducing the ECP of the stainless steel to values below −230 mV(SHE). An effective method of achieving this objective is to use HWC. However, high hydrogen additions, e.g., of about 200 ppb or greater, that may be required to reduce the ECP below the critical potential, can result in a higher radiation level in the steam-driven turbine section from incorporation of the short-lived N-16 species in the steam. For most BWRs, the amount of hydrogen addition required to provide mitigation of IGSCC of pressure vessel internal components results in an increase in the main steam line radiation monitor by a factor of five to eight. This increase in main steam line radiation can cause high, even unacceptable, environmental dose rates that can require expensive investments in shielding and radiation exposure control. Thus, recent investigations have focused on using minimum levels of hydrogen to achieve the benefits of HWC with minimum increase in the main steam radiation dose rates.

An effective approach to achieve this goal is to either coat or alloy the stainless steel surface with palladium or other noble metal. The presence of palladium on the stainless steel surface reduces the hydrogen demand to reach the required IGSCC critical potential of −230 mV (SHE). The techniques used to date for palladium coating include electroplating, electroless plating, hyper-velocity oxy-fuel, plasma deposition and related high-vacuum techniques. Palladium alloying has been carried out using standard alloy preparation techniques. These approaches are ex-situ techniques in that they cannot be practiced while the reactor is in operation. Also noble metal coatings such as those applied to plasma spraying and by hyper-velocity oxy-fuel must be applied to all surfaces that require protection, i.e., they afford no protection to adjacent uncoated regions.

The most critical requirement for IGSCC protection of Type 304 stainless steel is to lower its ECP to values below the protection potential, i.e., −230 mV (SHE). The manner in which this potential is achieved is immaterial, e.g., by alloying, doping or by any other method. It has been demonstrated that it is sufficient to dope the oxide film by the appropriate material (e.g., Pd) to achieve a state of lower ECP. It was shown in later work that a thickness of about 200 to 300 Å of the doping element (Pd) is sufficient to impart this benefit of lower potential at low hydrogen concentrations. This is not surprising because the ECP is an interfacial property, and hence modifying the interface by a process such as doping would alter its ECP. The critical requirement is that the dopant remain on the surface over a long period of time to gain the maximum benefit from the doping action.

U.S. patent application Ser. No. 08/635,593 discloses an innovative method of in situ application of noble metal onto stainless steel or other metal surfaces by injecting the high-temperature water that is in contact with the metal surface. That method dopes the oxide film with noble metal and provides sufficient catalytic activity for $H_2$ and $O_2$ recombination to reduce the ECP of the metal surfaces to required protection values. This approach of noble metal doping has been shown to be effective against crack initiation and crack growth in stainless steel at $H_2/O_2$ molar ratios >2 in the environment.

SUMMARY OF THE INVENTION

The present invention is a doping method for achieving the same objective of low ECPs without the addition of hydrogen. The method results in slow or no crack growth in stainless steel and other metals.

In one aspect, the invention provides a method for treating a metal component to mitigate cracking in a surface of the metal component during use in a water-cooled nuclear reactor or associated equipment. The method comprises forming an oxide film on the surface of the metal component and doping the oxide film with species of a non-noble metal. The species are incorporated in the oxide film and the electrochemical corrosion potential at the surface is reduced, thereby mitigating cracking.

In another aspect, there is provided method for mitigating general corrosion and initiation or propagation of a crack in a metal component having an oxided surface. The method includes the steps of immersing the metal component in a solution or suspension of a compound containing a non-noble metal, and causing the non-noble metal compound to decompose to release non-noble metal species which incorporate in said oxided surface.

Examples of metals forming the components to be treated are nickel-based alloys, cobalt-based alloys, titanium-based alloys, copper-based alloys and ferrous and non-ferrous alloys. Carbon steels and low alloy steels are further examples.

Examples of non-noble metals which may be used to dope the oxided metal components are zirconium, hafnium, niobium, tantalum, yttrium, ytterbium, tungsten, vanadium, titanium, molybdenum, chromium, cerium germanium and nickel. It is also possible to use suitable non-metals which possess conducting or semi-conducting properties, such as silicon or carbon.

The non-noble metals identified above can be used alone or in admixture with other non-noble metals or non-metals. For example, it is possible to use zirconium-niobium mixtures or zirconium in admixture with one or more of the elements present in Zircaloy-2, e.g. tin, iron, chromium and nickel, in the percentage amounts generally present in Zircaloy-2, i.e. tin—1.2–1.7%, iron—0.07–0.20%, chromium—0.05–0.15%, nickel—0.03–0.08% (see the Brief Description of the Drawings with particular reference to FIG. 2).

When the present invention is practiced, the metal corrosion potential is polarized in the negative direction without the addition of hydrogen. The invention is based on reducing the electrical conductivity of the protective oxide which forms naturally on the surfaces of components made of stainless steels and other metals in a light water nuclear reactor. The passive oxide films on structural materials comprise iron, nickel and chromium oxides, which are semiconducting in high-temperature water. Doping levels required to modify semiconducting behavior are typically low. This reduction in electrical conductivity forces the corrosion potential to be formed on the (inner) metal surface, not on the (outer) oxide-water interface. The poor access of oxidants in the bulk solution to the metal surface causes the corrosion potential to drop to a lower thermodynamic limit associated with deaerated water of a specific pH. Such modification of the oxide properties provides a very high degree of resistance to SCC even in the absence of any hydrogen addition.

The passive oxide films on the surfaces of structural materials can be doped with zirconium or other non-noble metals or non-metals such as those mentioned above using either in-situ or ex-situ techniques. In accordance with both techniques, the structural material is immersed in a solution or suspension of a compound containing a non-noble metal. The non-noble metal must have the property of increasing the corrosion resistance of the stainless steel or other metal surface when incorporated therein. The selected compound must have the property that it decomposes under reactor thermal conditions to release ions or atoms of the selected non-noble metal which incorporate in the oxide film formed on the stainless steel or other metal surfaces. As used in the claims hereinafter, the term "species" means ions or atoms.

Preferred compounds used in accordance with the invention are those containing zirconium, e.g., the organometallic compound zirconium acetylacetonate [$ZrAc_4$] and the inorganic compounds zirconium nitrate [$Zr(NO_3)_4$] and zirconyl nitrate [$ZrO(NO_3)_2$]. The compounds may be soluble or insoluble in water (i.e. may form solutions or suspensions in water). Similar organometallic or inorganic compounds of other non-noble metals listed above may be used, provided that they do not contain unacceptable anions. Examples of unacceptable anions are $F^-$, $Cl^-$, $Br^-$, $I^-$ and $SO_4^{2-}$.

The concentration of the non-noble metal is no higher than 2000 ppb, for example 0.1 to 1000 ppb, typically 1 to 500 ppb, more usually 2 to 100 ppb. in the reactor. When mixtures are used, in particular zirconium-niobium mixtures, it has been found that a combination of about 95–98 ppb of zirconium and 5–2 ppb niobium, for example about 96 ppb zirconium and about 4 ppb niobium, give good results over extended periods of time.

Upon injection of the solution or suspension of the non-noble metal compound, the compound decomposes and releases non-noble metal species which incorporate in the oxide film on the surfaces of metal components immersed in the water. For example, in the case where the alloy is stainless steel and the non-noble metal is zirconium, the zirconium is incorporated into the oxide film on the stainless steel surface via a thermal decomposition process of the zirconium compound. While not being bound by theory, it appears that zirconium ions or atoms replace iron, nickel and/or chromium atoms in the oxide film, resulting in a zirconium-doped oxide film. The oxide film is believed to include mixed nickel, iron and chromium oxides. It is possible also that some zirconium is deposited on the surface of the oxide film in the form of a finely divided metal. During deposition, zirconium will be deposited inside any existing cracks on the stainless steel surfaces. The zirconium deposits around the crack mouth region and into the interior of the crack.

This doping technique reduces the ECP of the stainless steel surfaces, particularly the interior surfaces of any crack, to below the critical threshold ECP. Thus, this approach should be effective against crack initiation and crack growth in stainless steel and other metals even in the absence of hydrogen in the high-temperature water environment.

Furthermore, rapid depletion of zirconium from the crack interior should not occur because of the low fluid flow experienced inside the crack even if the crack mouth is in a high fluid flow regime. This promises to be a significant advantage because crack mitigation would still be achievable even if bulk surface zirconium removal occurs under high fluid flow conditions.

The process of the present invention is distinguished from the processes of U.S. Pat. No. 5,130,080 and 5,130,081 to Niedrach. The Niedrach patents teach that it is possible to electrolessly plate oxide films using conventional electroless plating techniques. Conventional electroless plating is carried out at relatively low temperatures, typically in the region of 50 to 80° C., possibly lower, and requires the presence of an added reducing agent, typically sodium hypophosphite, to supply electrons for reduction of noble metal ions to the metal. The reaction takes place only on a catalytic surface which has been sensitized/activated beforehand, for example with stannous chloride, and the process results in a build-up of metal coating on the surface which eventually coats the entire surface with deposited metal. The electroless plating bath typically contains high ionic concentrations, of the order of thousands of ppm, of chemicals, including, for example, palladium (II) chloride, ammonium hydroxide, ammonium chloride, disodium EDTA and hydrazine, as well as a reducing agent (e.g. sodium hypophosphite). The pH of the electroless bath is usually in the region of 9.0 to 10.5 in view of the presence of base (ammonium hydroxide and ammonium chloride).

The process of the present invention does not rely on the use of electroless plating techniques or other techniques which result in the metal being plated on the oxide surface. In the present process, the non-noble metal compound or mixture of metal compounds is introduced into the high-temperature water in an amount such that the concentration of the metal(s) in the water is very low, i.e. in the ppb range, but is sufficient such that when present on the metal component, the ECP is lowered below the critical potential required for protection from stress corrosion cracking. As noted earlier, typically the metal compound is added in such an amount to produce a metal concentration of no higher than 2000 ppb, for example 0.1 to 1000 ppb, typically 1 to 500 ppb, more usually 2 to 100 ppb.

The compound solution or suspension is injected into the high-temperature water while the reactor is operating and generating nuclear heat. The temperature of the water when the reactor is operating is typically in the range of 150°–300° C., for example 190°–290° C., more usually about 288° C. When the compound meets the high-temperature water, it decomposes very rapidly and the non-noble metal species are incorporated in the oxide surface.

At the very low levels of metal(s) introduced into the reactor, the stainless steel oxide surface is not covered completely with metal. Typically, the doped surface has metal present in an amount of about 0.1–15 atomic %, for example 0.5–10 atomic %, more usually 2–5 atomic %.

The depth of metal in the doped surface is generally in the range of 100 to 1000 Angstroms, more usually 200 to 500 Angstroms. The external appearance of the doped oxided alloy treated according to the present process does not differ significantly from the appearance of untreated stainless steel oxide. The doped surface does not have a bright metallic luster as is generally obtained with electroplating or electroless coating processes.

In the present process, only the compound solution or suspension is injected into the high-temperature water. No reducing agents (including hydrogen), acids and bases, are added. As a result, the pH of the water at lower temperatures is in the region of 6.5 to 7.1, and at higher operating temperatures is lower, generally in the region of about 5.5–5.8, for example 5.65. This is due to increased dissociation of the water at the higher temperatures.

An operating BWR has very stringent coolant water conductivity levels which must be observed. Typically, the conductivity of the coolant water must not exceed 0.3 $\mu$S/cm, and more usually must be less than 0.1 $\mu$S/cm. Such conductivity levels are adversely impacted by high ionic concentrations of species, and every effort is made in the present process to ensure that reactor ionic concentrations of species are maintained as low as possible after clean-up. The process in particular excludes the use of chloride and sulfate ions in view of their corrosive nature.

The present process does not involve any catalytic activation/sensitization of the stainless steel oxide surface. The use of stannous chloride to achieve such activation would be incompatible with operation of the BWR and the stringent conductivity limits on the coolant water referred to above.

Following injection and incorporation of the metal(s) in the oxided stainless steel surfaces, the water is subjected to a conventional clean-up process to remove ionic materials such as nitrate ions present in the water. This clean-up process is usually carried out by passing a fraction of the water removed from the bottom head of the reactor and recirculation piping through an ion exchange resin bed, and the treated water is then returned to the reactor via the feedwater system.

In summary, the oxygen content of the reactor water can be reduced by injection of a non-noble metal compound alone initially into high temperature water to dope oxided stainless steel surfaces. Some oxygen will be reduced by the organics of the metal compound (e.g. an organometallic zirconium compound) following thermal decomposition or radiolytic decomposition (induced by gamma and neutron radiation) of the metal compound.

DETAILED DESCRIPTION OF THE PREFERRED EMBODIMENTS

Figure 1:
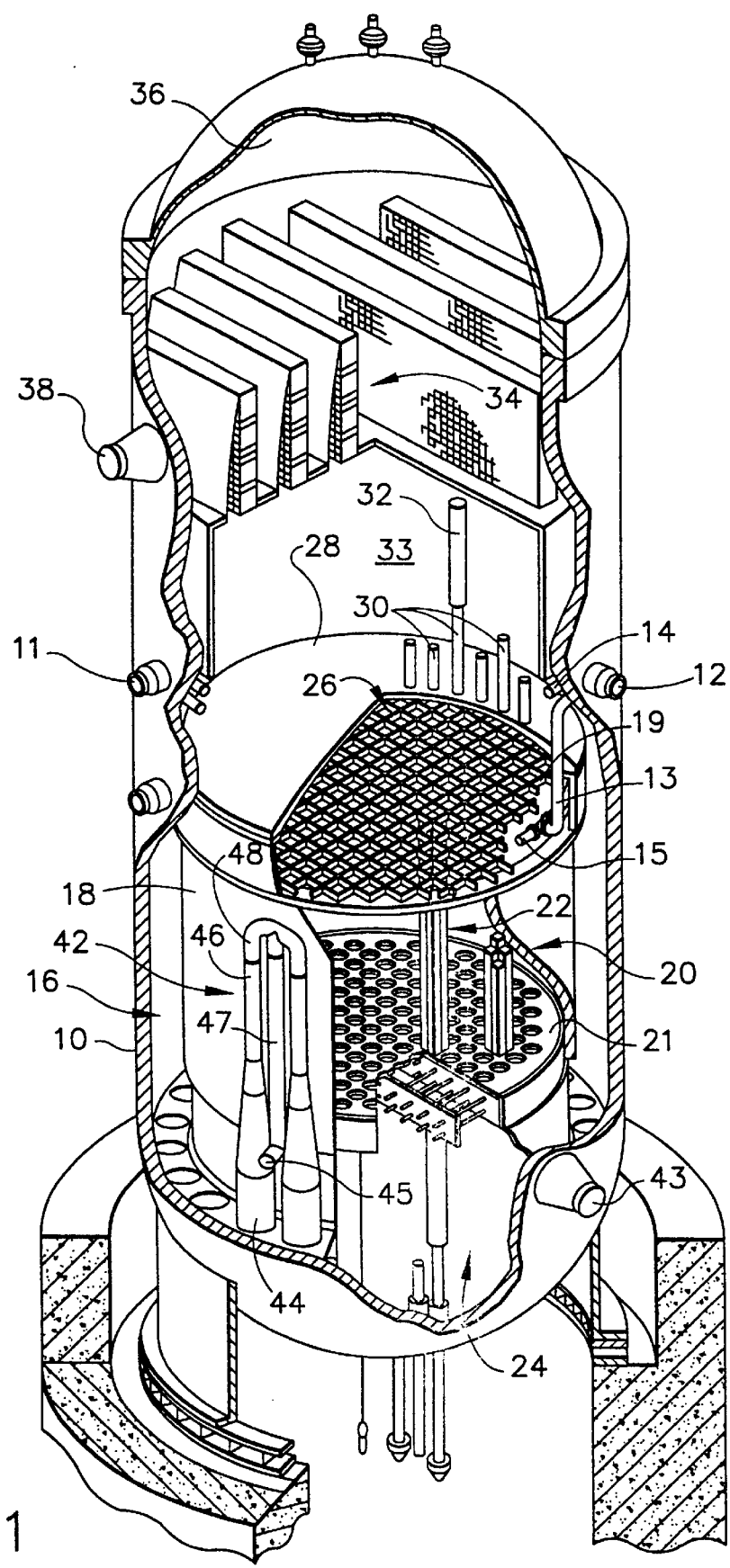
FIG. 1 is a schematic showing a partially cutaway perspective view of a conventional BWR.

The fluid flow in a boiling water reactor will be generally described with reference to FIG. 1. Feedwater is admitted into a reactor pressure vessel (RPV) 10 via a feedwater inlet 12 and a feedwater sparger 14, which is a ring-shaped pipe having suitable apertures for circumferentially distributing the feedwater inside the RPV. A core spray inlet 11 supplies water to a core spray sparger 15 via core spray line 13. The feedwater from feedwater sparger 14 flows downwardly through the downcomer annulus 16, which is an annular region between RPV 10 and core shroud 18. Core shroud 18 is a stainless steel cylinder which surrounds the core 20 comprising numerous fuel assemblies 22 (only two 2×2 arrays of which are depicted in FIG. 1). Each fuel assembly is supported at the top by top guide 19 and at the bottom by core plate 21. Water flowing through downcomer annulus 16 then flows to the reactor lower plenum 24.

The water subsequently enters the fuel assemblies 22 disposed within core 20, wherein a boiling boundary layer (not shown) is established. A mixture of water and steam enters reactor upper plenum 26 under shroud head 28. Reactor upper plenum 26 provides standoff between the steam-water mixture exiting core 20 and entering vertical standpipe 30, which are disposed atop shroud head 28 and in fluid communication with reactor upper plenum 26.

The steam-water mixture flows through standpipes 30 and enters steam separators 32, which are of the axial-flow centrifugal type. The separated liquid water then mixes with feedwater in the mixing plenum 33, which mixture then returns to the core via the downcomer annulus and/or through jet pump assemblies. The steam passes through steam dryers 34 and enters steam dome 36. The steam is withdrawn from the RPV via steam outlet 38.

The BWR also includes a coolant recirculation system which provides the forced convection flow through the core necessary to attain the required power density. A portion of the water is sucked from the lower end of the downcomer annulus 16 via recirculation pump (not shown) into jet pump assemblies 42 (only one of which is shown) via recirculation water inlets 45. The BWR has two recirculation pumps, each of which provides the driving flow for a plurality of jet pump assemblies. The pressurized driving water is supplied to each jet pump nozzle 44 via an inlet riser 47, an elbow 48 and an inlet mixer 46 in flow sequence. A typical BWR has 16 to 24 inlet mixers.

The present invention is a technique to dope stainless steel and other metal surfaces (including the interiors of cracks formed therein) inside a BWR with zirconium, titanium or other non-noble metal. In accordance with an in situ technique, this is accomplished by injecting an inorganic or organometallic compound containing zirconium, titanium or other non-noble metal into the high-temperature water of the BWR during shutdown or during operation. The invention will be disclosed with specific reference to doping of stainless steel surfaces with zirconium. However, it should be understood that other non-noble metals (such as hafnium, niobium, tantalum, yttrium, ytterbium, tungsten, vanadium, titanium, molybdenum, chromium, cerium and nickel, as well as suitable nonmetals which possess conducting or semi-conducting properties, such as silicon, carbon or germanium) can be used in place of zirconium; and that the surfaces of components made of alloys other than stainless steel (e.g., nickel-based alloys, cobalt-based alloys, titanium-based alloys, copper-based alloys, and ferrous and non-ferrous based alloys, as well as carbon steels, low alloy steels, etc.) can be doped to achieve reduced ECPs using the method of the present invention.

Preferably the zirconium compound is injected at a point upstream of the feedwater inlet 12 (see FIG. 1) or downstream of the recirculation pumps. The high temperature as well as the gamma and neutron radiation in the reactor core act to decompose the compound, thereby releasing Zr species for incorporation into the oxide film which coats oxidized stainless steel surfaces in a BWR. Examples of Zr-containing compounds which can be used for this purpose are the zirconium compounds containing nitrate groups, such as zirconyl nitrate [$ZrO(NO_3)_2$] and zirconium nitrate [$Zr(NO_3)_4$]. Another Zr-containing compound which can be used is zirconium acetylacetonate [$ZrAc_4$].

It is known that palladium doping combined with hydrogen addition is effective in mitigating IGSCC cracking. The action of palladium doping is to cause very efficient recombination of added $H_2$ with $O_2$ present in the system such as in an operating BRNR, so that the local $O_2$ levels are considerably reduced. The metal surface (e.g., Type 304 stainless steel) in effect sees much less $O_2$ even though the bulk fluid may have a much higher $O_2$ content. The lowering of surface $O_2$ (i.e., at the interface) is sufficient to bring about the necessary ECP change. The amount of $H_2$ required to achieve the protection potential, even if the metal surface were doped with palladium, depends to a large extent on the specific nature of the plant. As an example, in the case of a high-power-density plant, such as a BWR 4, the required hydrogen may be relatively small so that the main steam line radiation levels may still remain at the background level. However, for a low-power-density plant, such as a BWR 3, where recombination of the $H_2$ and $O_2$ in the downcomer region is not as efficient, more $H_2$ may be required to achieve IGSCC protection. Thus, although palladium doping helps, the benefit may not be as much as it would otherwise be if it were a high-power-density plant. Thus, in such situations, even with palladium doping, the required $H_2$ levels may be sufficiently high to bring the main steam line radiation levels above the background level. On the other hand, if an element existed that could lower the ECP without the addition of hydrogen, then that would be a great benefit, because the question of increasing the main steam line radiation level does not arise. It is in this context that zirconium doping was viewed as a possible alternative to palladium doping, particularly based on observations of the ability of Zr—Nb alloy to lower the ECP of a Type 304 stainless steel CERT specimen.

ECP and $O_2$ test data at 547° F. for a Type 304 stainless steel CERT specimen held in place in a levis using oxidized Zr—Nb pins, a Type 304 stainless steel electrode tip and a Type 304 stainless steel CERT specimen held in levis using $ZrO_2(MgO)$ ceramic pins are compared in Table 1. Al stainless steel specimens had been pre-oxidized before the test.

TABLE 1

| Specimen | $O_2$ (ppb) | ECP (mV, SHE) |
| --- | --- | --- |
| 304 SS (CERT) with oxidized Zr-Nb pins | 225 | −196 |
| 304 SS electrode tip | 225 | +60 |
| 304 SS (CERT) with $ZrO_2$ (MgO) pins | 235 | +90 |

A constant extension rate tensile (CERT) test was performed at 547° F. with a Type 304 stainless steel specimen. The specimen was held in the clevis of a standard CERT autoclave using oxidized Zr—Nb pins. During the test it was discovered that the ECP of the stainless steel specimen was far more negative (−196 mV/SHE) than expected at the oxygen level (225 ppb $O_2$) used in the study. A preoxidized Type 304 stainless steel electrode tip that was in the same autoclave showed a potential of +60 mV(SHE), which was anticipated in the high-oxygen environment used. Based on this result, it was concluded that the oxide film formed on the Zr—Nb pin cracked under the load during the CERT test, which exposed the bare zirconium/niobium metal that contacted the Type 304 stainless steel specimen. This caused a mixed potential to be established at the stainless steel specimen dominated by the negative potential of the Zr—Nb alloy material. Thus, the Type 304 stainless steel CERT specimen showed a negative potential of −196 mV(SHE) instead of showing a positive potential at 225 ppb $O_2$. This observation is consistent with the finding that Zircaloy-2 and Zircaloy-4 also show very negative potentials of −820 mV(SHE) at 550° F. in 8 ppm $NaNO_3$ in the presence of 248 ppb $O_2$, as shown in FIG. 2.

Figure 2:
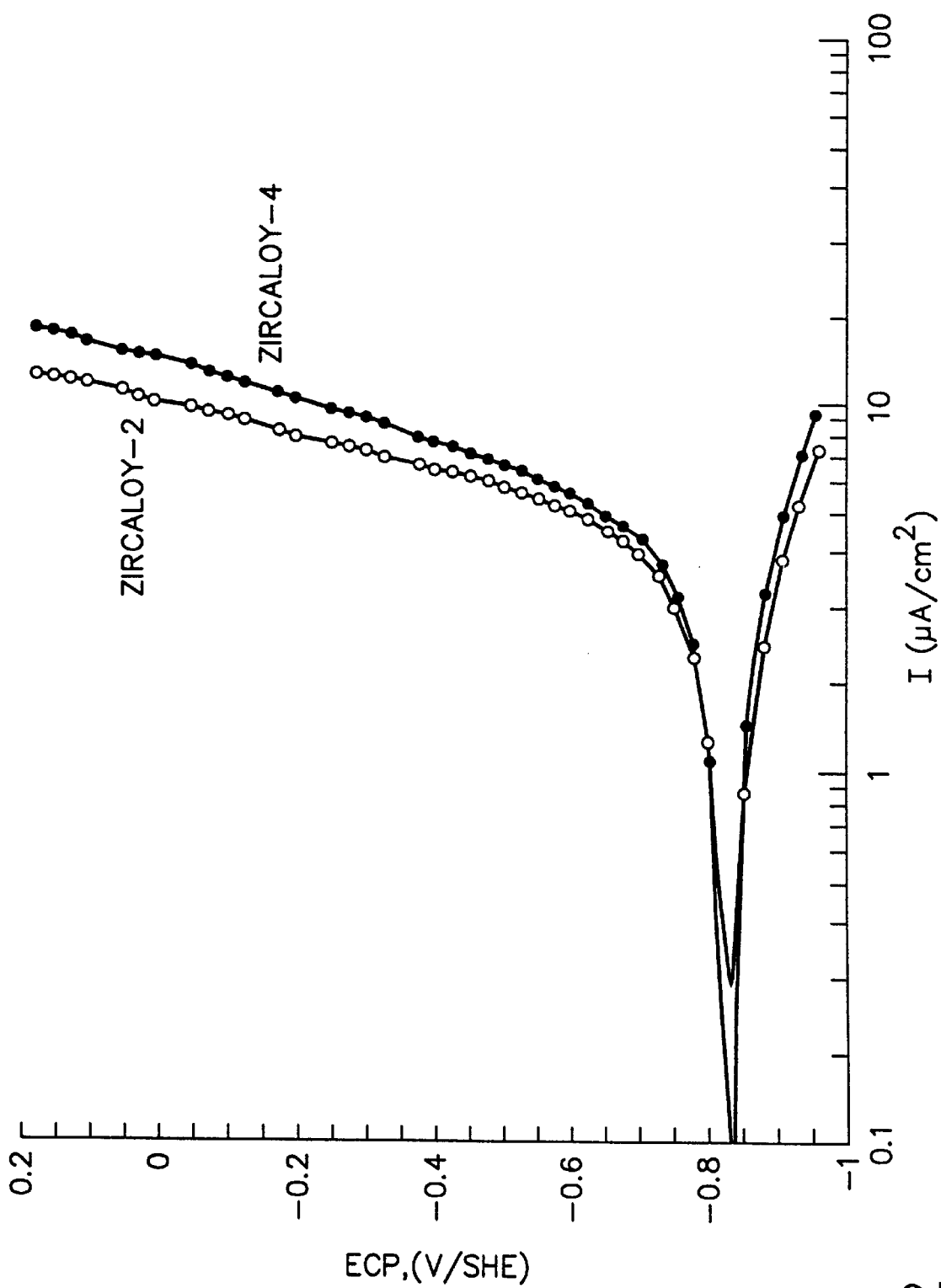
FIG. 2 is a plot of polarizing curves for Zircaloy-2 and Zircaloy-4, illustrating a low corrosion potential of −820 mV(SHE) in a 8 ppm $NaNO_3$ in the absence of any added hydrogen. Zircaloy is an alloy of zirconium with small amounts of iron, tin and other alloying elements. In particular, Zircaloy-2 contains: tin—1.2–1.7%, iron—0.07–0.20%, chromium—0.05–0.15%, nickel—0.03–0.08%, other elements—270 ppm maximum; and Zircaloy-4 contains: tin—1.2–1.7%, iron—0.12–0.18%, chromium—0.05–0.15%, nickel—0.007% maximum, other elements—270 ppm maximum.

FIG. 2 is a plot of polarization curves for Zircaloy-2 and Zircaloy-4 illustrating a low corrosion potential of −820 mV(SHE) in 8 ppm $NaNO_3$ at 289° C. in the absence of any added $H_2$, i.e., having only an oxygen level of 248 ppb $O_2$. FIG. 2 indicates that if the metal surface incorporates an insulating film such as that formed by zirconium or one of its alloys, then it is possible to achieve very low ECPs without adding any $H_2$. Thus, in principle, because of the low ECPs, it should be possible to mitigate IGSCC of susceptible alloys such as Type 304 stainless steel, nickel alloys and other steels by doping the alloy surface with a metallic element such as zirconium, so that the surface behaves more like a zirconium surface, resulting in a lower ECP. Zirconium doping of stainless steel surfaces could be achieved using zirconium compounds such as zirconium acetylacetonate, zirconyl nitrate [$ZrO(NO_3)_2$] and zirconium nitrate [$Zr(NO_3)_4$]. Other dopants that can potentially be used for generating similar insulating or semiconducting surfaces include, for example, hafnium, niobium, tantalum, yttrium, ytterbium, tungsten, vanadium, titanium, molybdenum, chromium, cerium and nickel, as well as suitable non-metals which possess conducting or semiconducting properties, such as silicon, carbon or germanium.

Thus, when a metal such as stainless steel is ohmically shunted to a zirconium-containing alloy, the potential of the stainless steel polarizes in the negative direction as observed in the above study. The exact potential to which stainless steel polarizes depends upon the area ratio of the zirconium/stainless steel and the electrochemical activity of the particular zirconium alloy itself. The fact that the Zr—Nb pins in fact are polarizing the Type 304 stainless steel CERT specimen potential in the negative direction was proven by replacing the Zr—Nb pins with ceramic ($ZrO_2(MgO)$) pins, which eliminated the mixed potential effect, and resulted in a positive potential (+90 mV(SHE) for stainless steel CERT specimen, as expected.

An important benefit of this observation is the ability to achieve required IGSCC protection potentials for Type 304 stainless steel, either by shunting the Type 304 stainless steel to zirconium or one of its alloys (electrochemically short range), or by doping the stainless steel surface with zirconium or one of its alloys. Zirconium doping of stainless steel (or other metal) components of a BWR by injecting a zirconium compound into the high-temperature water would make it possible to polarize the stainless steel potential in the negative direction without using hydrogen. The benefits of this achievement would be numerous. First, the main steam radiation dose rates should remain at the background level because no hydrogen will be used. Second, zirconium and its alloys are compatible with fuel cladding material and hence fuel removal may not be required during zirconium doping. Lastly, the cost of zirconium is much less than the cost of palladium.

In accordance with the invention, zirconium doping can be performed in situ either during shutdown (when the water temperature inside the reactor is about 40°–60° C.) or during operation (when the water temperature inside the reactor is about 288° C.). As a result of injecting the solution of zirconium compound into the feedwater, all structural reactor components can be treated ex situ before installation in the reactor.

An experiment was performed to test the effect on corrosion potential of exposing Type 304 stainless steel to a $ZrO(NO_3)_2$ solution. Test specimens of Type 304 stainless steel (⅛" diam.×2" long) were pre-oxidized in 288° C. water containing 200 ppb oxygen for 1 week and then immersed in an ultrasonic bath containing a 1 mM $ZrO(NO_3)_2$ solution, open to air, at 60° C. for 10 and 20 days respectively.

Figure 3:
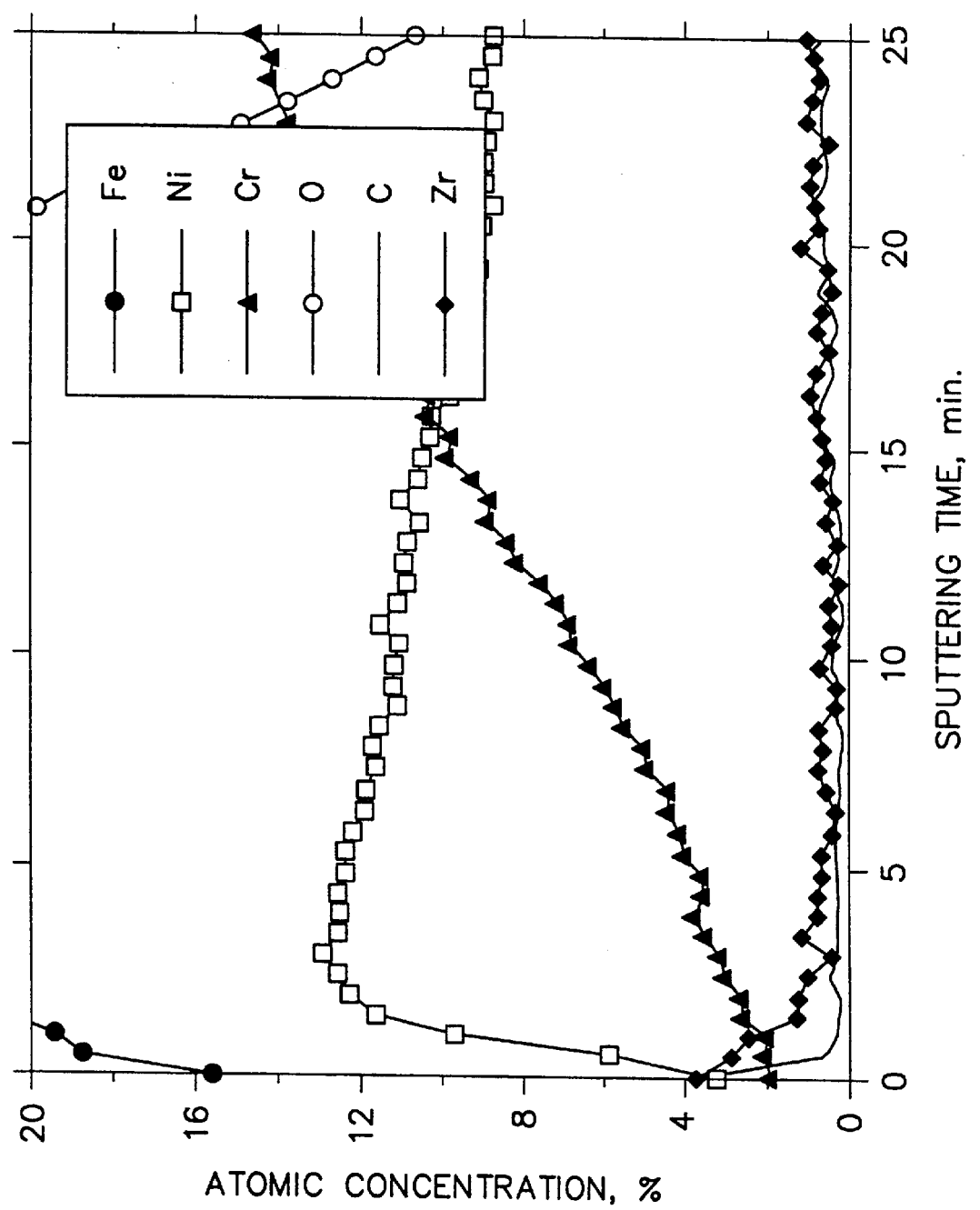
FIG. 3 is an Auger electron spectroscopy depth profile of the surface of Type 304 stainless steel after exposure to a 1 mM $ZrO(NO_3)_2$ solution at 60° C. for 10 days, showing that zirconium has been incorporated into the oxide film.

FIG. 3 shows an Auger electron spectroscopy depth profile of the surface of Type 304 stainless steel after exposure to a 1 mM $ZrO(NO_3)_2$ solution at 60° C. for 10 days. The data in FIG. 3 confirm that zirconium has been incorporated into the oxide film as a result of the treatment in accordance with the invention. Zirconium was incorporated into the oxide film to a depth of 300 Å (1 minute sputtering time ≈100 Å).

Figure 4:
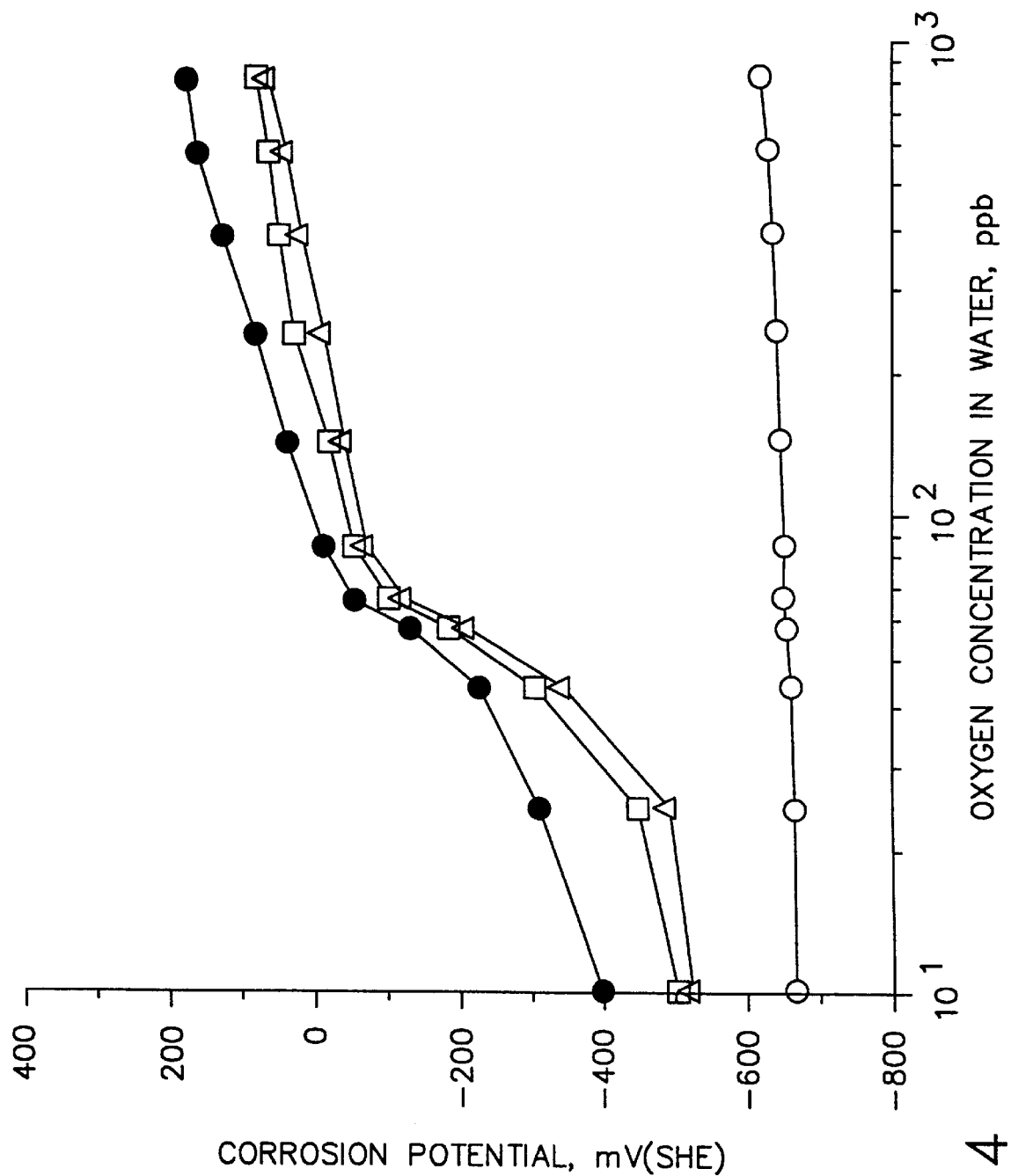
FIG. 4 is a graph showing corrosion potential measurements for electrodes in 288° C. water containing various amounts of oxygen, the electrodes being respectively made from Type 304 stainless steel (●), Type 304 stainless steel doped with zirconium by immersion in a zirconyl nitrate solution for 10 days (□) and 20 days (▲), and pure zirconium (○).

The corrosion potentials of the Zr-doped Type 304 stainless steel test specimens, as well as undoped and pure zirconium test specimens, were measured in 288° C. water containing various amounts of oxygen. All test specimens were exposed to 288° C. pure water for 2 days and the corrosion potentials were sequentially measured with incremental additions of oxygen. The experimental data is shown in FIG. 4 for Type 304 stainless steel (●), Type 304 stainless steel treated with a 1 mM $ZrO(NO_3)_2$ solution for 10 days (□) and 20 days (▲), and pure zirconium (○) electrodes.

It was observed that the Zr-doped Type 304 stainless steel test specimens showed lower corrosion potentials than the undoped specimens at the same oxygen level. This difference in the corrosion potentials of the Zr-doped and undoped stainless steel electrodes is attributable to the change in the electrical conductivity of the oxide film caused by doping of zirconium into the oxide. By contrast, the corrosion potential of pure zirconium was about −650 mV(SHE), even at high oxygen levels. As seen in FIG. 4, the corrosion potential of Zr-doped Type 304 stainless steel is further reduced as the duration of the doping treatment is increased from 10 days to 20 days.

Another experiment was performed to test the effect on corrosion potential of exposing Type 304 stainless steel to a zirconium acetylacetonate solution. The Type 304 stainless steel specimen was treated with 100 ppb Zr added as zirconium acetylacetonate in high-temperature water (550° F.) over a period of 48 hr.

An exemplary zirconium acetylacetonate injection solution was prepared by dissolving 52.6 mg of zirconium acetylacetonate powder in 40 ml of ethanol. The ethanol solution was then diluted with water. After dilution, 10 ml of ethanol are added to the solution. This solution is then diluted with water to a volume of 1 liter. Obviously, the concentration range can be varied. Alternatively, a water-based suspension can be formed, without using ethanol, by mixing zirconium acetylacetonate powder in water. As used in the claims hereinafter, the term "solution" means solution or suspension.

Figure 5:
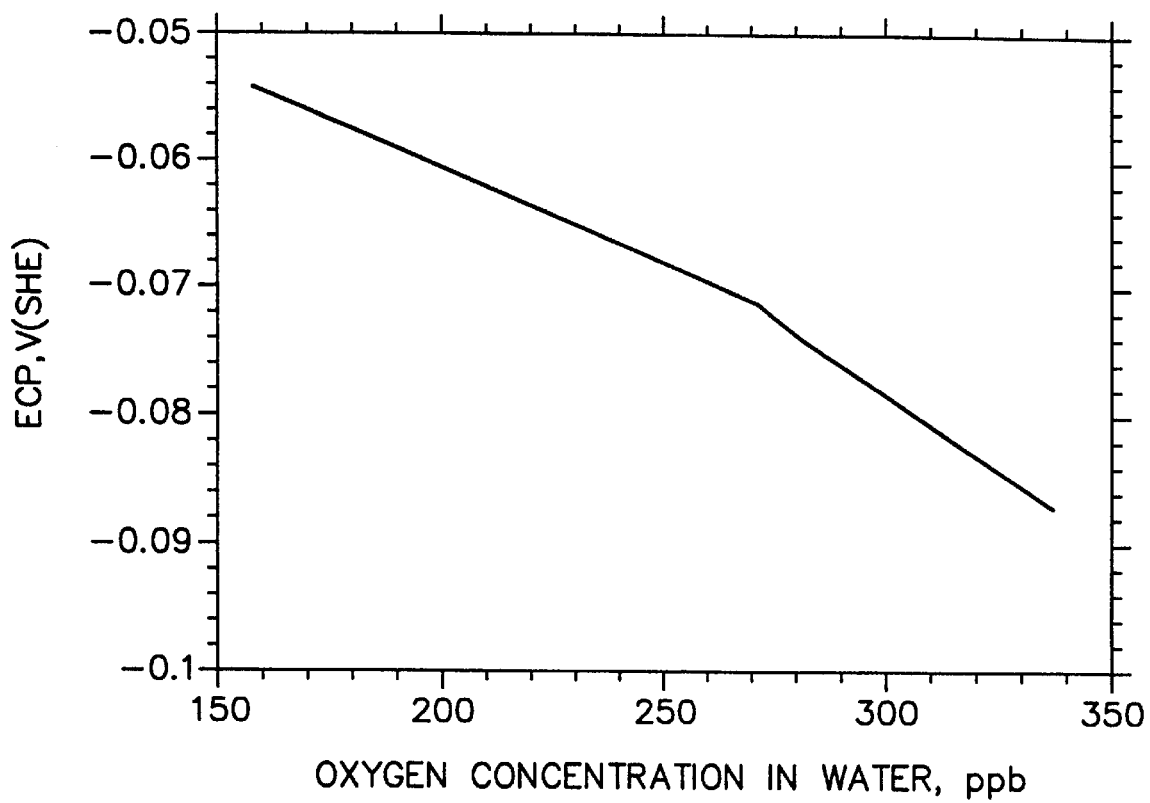
FIG. 5 is a graph showing corrosion potential measurements for electrodes in 550° F. water containing various amounts of oxygen, the electrodes being made from Type 304 stainless steel doped with zirconium by immersion in a zirconium acetylacetonate solution for 48 hr.

The zirconium acetylacetonate compound, dissolved in the ethanol/water mixture, was injected into the inlet side of the main pump in the flow loop using an injection pump at a rate so that the solution entering the autoclave (at 550° F.) had a Zr concentration of ~100 ppb. The results of this experiment are depicted in FIG. 5.

After doping with zirconium by the above procedure, the corrosion potential of the Type 304 stainless steel specimen was tested in high-temperature water at 550° F. The response of the Zr-doped specimen was tested at different oxygen levels. FIG. 5 shows that the ECP of the Zr-doped specimen was negative from the outset even in the presence of high oxygen levels. As the oxygen content was increased, the ECP decreased, which is the reverse of the effect which would be seen in undoped Type 304 stainless steel. This may be partly due to the consumption of oxygen by the deposited organics, causing a local reduction in oxygen around the stainless steel surface. This indicates that even in the absence of any hydrogen, the presence of zirconium on and in the oxide film has a beneficial influence in providing lower ECPs.

As an example of the foregoing, the ECP of an undoped Type 304 stainless steel specimen pre-oxidized in 8 ppm $O_2$ for one week at 550° F. drops to a value of only −39 mV(SHE) even when the $H_2/O_2$ molar ratio is increased to 8.5. In contrast, the Type 304 stainless steel specimen doped using zirconium acetylacetonate shows a negative potential of −87 mV(SHE) at a dissolved oxygen concentration of 338 ppb without any hydrogen. Thus, zirconium doping of the stainless steel surface is extremely beneficial in reducing the ECP of the specimen and hence in controlling crack initiation and growth in stainless steel, since ECP is a primary factor that controls SCC of stainless steel and other alloys used in a nuclear reactor.

The foregoing method has been disclosed for the purpose of illustration. Variations and modifications of the disclosed method will be readily apparent to practitioners skilled in the art of mitigating stress corrosion cracking in metals and alloys. For example, the non-noble metals identified above as being useful in the invention can be used alone or in admixture with other non-noble metals or non-metals, as described above. Also the doping technique of the invention is not restricted to use with stainless steel surfaces, but also has application in reducing the ECP of other metals which are susceptible to IGSCC, such as those listed above and including e.g., nickel-based alloys, cobalt-based alloys, titanium-based alloys, copper-based alloys, ferrous alloys, non-ferrous alloys, carbon steel and low alloy steels. An alternative application technology includes having the metal compound as pressed pellets in a basket hung inside the reactor at different locations and operating the reactor with pump heat until metal doping occurs. Another approach would be to inject the compound locally into areas that have a higher susceptibility to IGSCC. All such variations and modifications are intended to be encompassed by the claims set forth hereinafter.

What is claimed is:

1. A method for treating a metal component to mitigate cracking in a surface of said metal component during use in a water-cooled nuclear reactor or associated equipment, comprising the steps of:

forming an oxide film on said surface of said metal component; and doping said oxide film with species selected from the group consisting of a non-noble metal and a non-metal which is conductive or semi-conductive whereby said species are incorporated in said oxide film to reduce the electrochemical corrosion potential of said surface and thereby mitigate cracking.

2. The method as defined in claim 1, wherein said non-noble metal is selected from the group consisting of zirconium, hafnium, tantalum, niobium, yttrium, ytterbium, tungsten, vanadium, titanium, molybdenum, cerium, chromium, nickel and germanium.

3. The method as defined in claim 1, wherein said compound is added to said reactor water in an amount sufficient to produce a non-noble metal concentration of 0.1 to 1,000 ppb.

4. The method as defined in claim 1, wherein said non-noble metal is present in said oxide film in an amount of 0.1–15 atomic %.

5. The method as defined in claim 1, wherein a mixture of non-noble metals is used.

6. The method as defined in claim 5, wherein said mixture comprises zirconium in association with an element selected from the group consisting tin, iron, chromium and nickel.

7. The method as defined in claim 5, wherein a mixture of zirconium and niobium is used.

8. The method as defined in claim 1, wherein said doping step is performed by immersing said oxide film in a solution of a non-noble metal-containing compound.

9. The method as defined in claim 8, wherein said non-noble metal-containing compound is selected from the group consisting of zirconium acetylacetonate, zirconium nitrate and zirconyl nitrate.

10. The method as claimed in claim 1, wherein said doping step is performed by injecting a solution of a thermally decomposable compound containing said non-noble metal into the water of said reactor while said water is being recirculated during shutdown of said reactor.

11. The method as defined in claim 1, wherein said doping step is performed by injecting a solution of a thermally decomposable compound containing said non-noble metal into the water of said reactor during normal operation of said reactor.

12. The method as defined in claim 1, wherein said metal component is made of an alloy selected from the group consisting of stainless steel, nickel-based alloy, cobalt-based alloy, titanium-based alloy, copper-based alloy, a ferrous alloy, a non-ferrous alloy, carbon steel and low alloy steel.

13. The method as defined in claim 1, wherein said oxide film is doped with said non-noble metal to a doping level sufficient to decrease the electrochemical corrosion potential on said metal component surface or inside a crack formed in said metal component surface to a level below the critical potential required to protect against intergranular stress corrosion cracking without the addition of hydrogen.

14. The method as defined in claim 1, wherein said non-metal is selected from the group consisting of silicon and carbon.

15. A method for mitigating general corrosion and initiation or propagation of a crack in a metal component having an oxidized surface, comprising the steps of:

immersing said metal component in a solution or suspension of a compound containing a non-noble metal or non-metal which is conductive or semi-conductive; and causing said non-noble metal compound or non-metal compound to decompose to release non-noble metal or non-metal species which incorporate in said oxided surface.

16. A method as defined in claim 15, wherein said non-noble metal is selected from the group consisting of zirconium, hafnium, tantalum, niobium, yttrium, ytterbium, tungsten, vanadium, titanium, molybdenum, cerium, chromium, nickel and germanium.

17. The method as defined in claim 15, wherein said non-noble metal-containing compound is selected from the group consisting of zirconium acetylacetonate, zirconium nitrate and zirconyl nitrate.

18. The method as defined in claim 15, wherein said immersing step is performed by injecting a solution of a thermally decomposable compound containing said non-noble metal into the water of a reactor while said water is being recirculated during shutdown of said reactor.

19. The method as defined in claim 18, wherein said immersing step is performed by injecting a solution of a thermally decomposable compound containing said non-noble metal into the water of said reactor during normal operation of said reactor.

20. The method as defined in claim 15, wherein said metal component is made of an alloy selected from the group consisting of stainless steel, nickel-based alloy, cobalt-based alloy, titanium-based alloy, copper-based alloy, ferrous and non-ferrous alloys, carbon steel and low alloy steel.

21. The method as defined in claim 15, wherein said oxided surface is doped with said non-noble metal to a doping level sufficient to decrease the electrochemical corrosion potential on said metal component surface or inside a crack formed in said metal component surface to a level below the critical potential required to protect against intergranular stress corrosion cracking when said metal component is installed in a water-cooled nuclear reactor without the addition of hydrogen.

22. The method as defined in claim 15, wherein said non-metal is selected from the group consisting of silicon and carbon.

\* \* \* \* \*